(12) United States Patent
Itoh

(10) Patent No.: US 7,977,100 B2
(45) Date of Patent: Jul. 12, 2011

(54) PUNCHING METHOD FOR USE IN DISPENSING

(75) Inventor: Teruaki Itoh, Kumamoto (JP)

(73) Assignee: IDS Company, Ltd., Kumamoto-shi, Kumamoto (JP)

( * ) Notice: Subject to any disclaimer, the term of this patent is extended or adjusted under 35 U.S.C. 154(b) by 0 days.

(21) Appl. No.: 12/487,200

(22) Filed: Jun. 18, 2009

(65) Prior Publication Data

US 2009/0257916 A1 Oct. 15, 2009

Related U.S. Application Data

(62) Division of application No. 11/057,247, filed on Feb. 15, 2005, now abandoned.

(30) Foreign Application Priority Data

Feb. 19, 2004 (JP) ................................. 2004-043055

(51) Int. Cl.
*G01N 35/02* (2006.01)

(52) U.S. Cl. .......... 436/47; 422/500; 422/509; 422/560; 422/561; 422/562; 422/568; 422/570; 83/360; 83/401; 83/404; 83/405

(58) Field of Classification Search ................... 422/62, 422/63, 67, 99, 100, 104, 500, 509, 560, 422/561, 562, 568, 570; 436/43, 47, 49, 436/54, 180; 83/360, 365, 401, 404, 405, 83/667, 669
See application file for complete search history.

(56) References Cited

U.S. PATENT DOCUMENTS

| | | | |
|---|---|---|---|
| 4,567,797 A | 2/1986 | Folk | |
| 4,974,457 A | 12/1990 | Angst et al. | |
| 5,318,420 A | 6/1994 | Blaimschein | |
| 5,355,755 A | 10/1994 | Sakata et al. | |
| 5,935,523 A | 8/1999 | McCandless et al. | |
| 6,148,710 A | 11/2000 | Pottorff | |
| 6,510,773 B1 | 1/2003 | Hart et al. | |
| 6,627,156 B1 | 9/2003 | Goodale et al. | |

*Primary Examiner* — Jill Warden
*Assistant Examiner* — Dwayne K Handy
(74) *Attorney, Agent, or Firm* — Nixon & Vanderhye P.C.

(57) ABSTRACT

Provided is a punching apparatus for use in dispensing, having a blood specimen contained therein, and punching a dispensing hole in a plug body of a test tube serving as a specimen container closed by the plug body whose upper end opening is made of a rubber or synthetic resin material, the apparatus comprising a guide rail serving as a transport passage which transports the test tube while the plug body thereof is held at the upper side in a vertical state, an elevating mechanism provided at a punch position P in the middle of the guide rail, and an ultrasonic cutter which is supported by the elevating mechanism, and which is lowered when the test tube reaches the punch position, thereby punching a dispensing hole immediately before penetrating the plug body from a top face thereof.

4 Claims, 2 Drawing Sheets

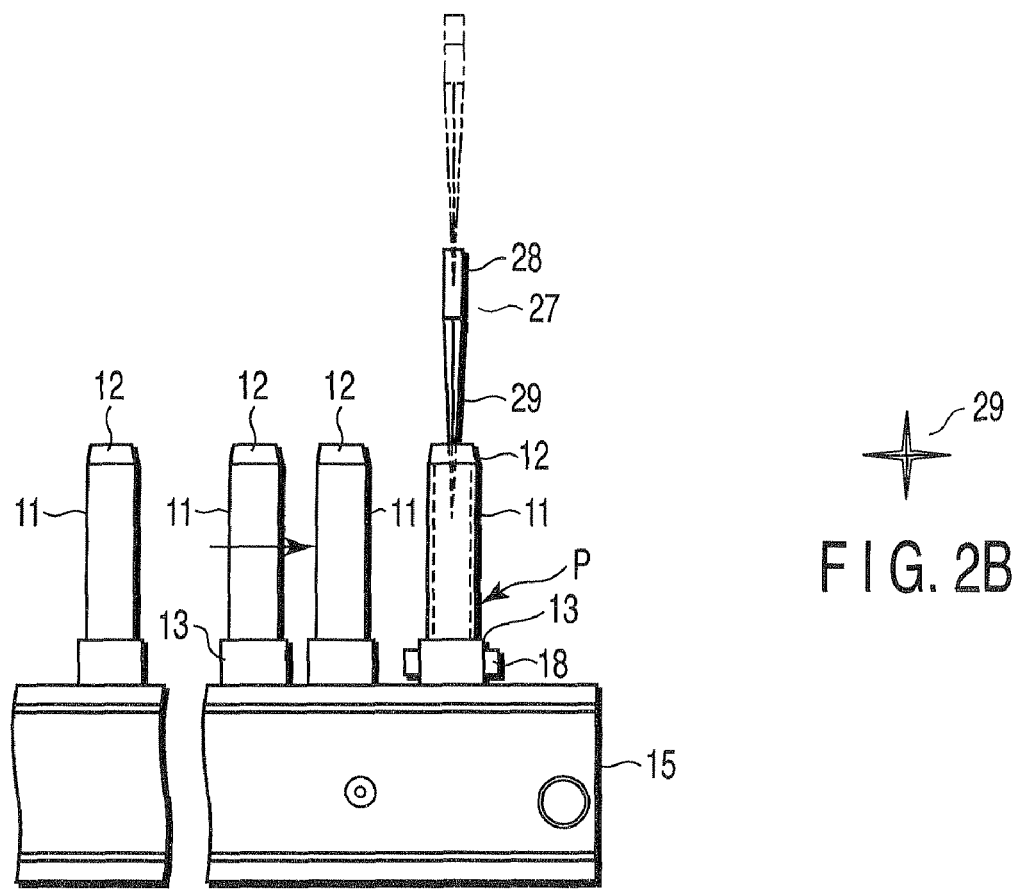
FIG. 2A
FIG. 2B
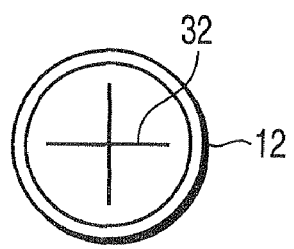
FIG. 3A
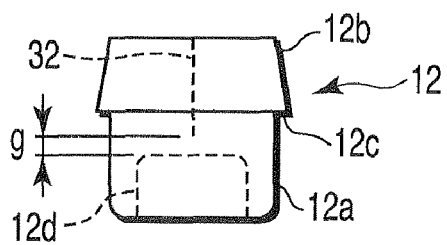
FIG. 3B

PUNCHING METHOD FOR USE IN DISPENSING

CROSS-REFERENCE TO RELATED APPLICATIONS

This application is a divisional of U.S. patent application Ser. No. 11/057,247, filed Feb. 15, 2005, now abandoned, which claims the benefit of priority from prior Japanese Patent Application No. 2004-043055, filed Feb. 19, 2004, the entire contents of each of which are incorporated herein by reference.

BACKGROUND OF THE INVENTION

1. Field of the Invention

The present invention relates to a punching apparatus for use in dispensing, the apparatus carrying out punching used for dispensing in a plug body of a sample container such as a test tube having a specimen such as a blood contained therein.

2. Description of the Related Art

A test tube for containing a sample such as blood is made of a transparent glass, and a plug body made of a rubber or a synthetic resin is mounted on an upper end opening of the test tube. In order to carry out sampling or dispensing of the specimen contained in the test tube, the test tube is held in a test tube holder in a vertical state for the purpose of transportation to each processing section, and the test tube holder is guided to a transport passage, thereby carrying out transportation.

For example, in specimen preprocessing transportation (clinical inspection), after centrifugal separation, the plug body of the test tube is opened by a plug opening mechanism. Then, the test tube is transported to a next process, and the blood specimen inside the test tube is sampled and dispensed by a dispensing mechanism.

However, there is a problem that a time loss occurs in opening all the plug bodies of a number of test tubes in the middle of transport, and impurities or the like are likely to enter the inside of the test tube during transport when the opened test tube is transported. Because of this, the plug body is punched by a punch needle of a punching apparatus for use in dispensing without opening the plug body of the test tube.

However, when the plug body is punched by means of the punch needle of the punching apparatus for use in dispensing without opening the plug body of the test tube, the plug body is punched by penetration by the punch needle. Thus, there is the inconvenience that chips of the plug body drop inside of the test tube, and the dropped chips are mixed in the internal blood specimen.

In addition, the chips of the plug body adhere to the punch needle of the punching apparatus for use in dispensing, thus making it necessary to wash the punch needle every time punching is carried out. Thus, there is a circumstance that equipment becomes complicated, and the punching process is low in efficiency.

BRIEF SUMMARY OF THE INVENTION

The present invention has been made in order to solve the foregoing problem. It is an object of the present invention to provide a punching apparatus for use in dispensing, the apparatus simplifying equipment configuration, and being capable of efficiently carrying out punching.

According to an aspect of the present invention, there is provided a punching apparatus for use in dispensing, having a blood specimen housed therein, and punching a dispensing hole on a plug body of a specimen container closed by the plug body which is made of a rubber or synthetic resin material at an upper end opening of the specimen container, the apparatus comprising: a transport passage which transports the specimen container while the plug body thereof is held at the upper side; an elevating mechanism provided at a punch position in the middle of the transport passage; and an ultrasonic cutter which is supported by the elevating mechanism, and which is lowered when the specimen container reaches the punch position, thereby punching a dispensing hole immediately before penetrating the plug body from the top face thereof.

According to the present invention, an ultrasonic cutter punches a dispensing hole immediately before penetrating a plug body of a specimen container. Therefore, equipment can be simplified and punching can be efficiently carried out without washing the ultrasonic cutter every time punching is carried out.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a side view showing the punching apparatus for use in dispensing;

FIG. 2B is an enlarged sectional view showing a blade portion of an ultrasonic cutter incorporated in the punching apparatus for use in dispensing;

FIG. 3A is a plan view showing a plug body targeted to be applied by the punching apparatus for use in dispensing; and FIG. 3B is a side view showing the plug body.

DETAILED DESCRIPTION OF THE INVENTION

Figure 1:
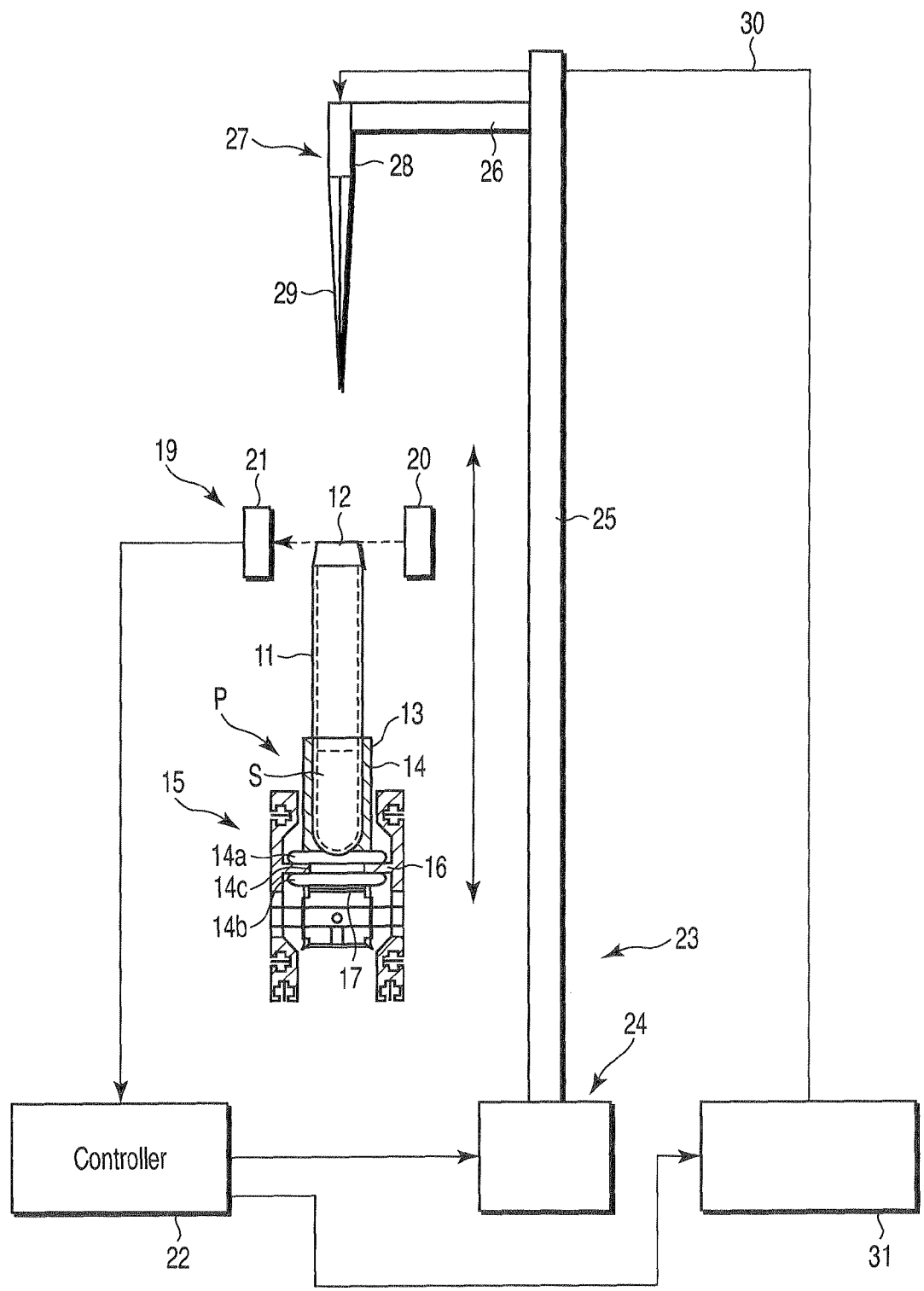
FIG. 1 is a front view showing a punching apparatus for use in dispensing according to an embodiment of the present invention.

FIG. 1 is a plan view showing a punching apparatus for use in dispensing according to one embodiment of the present invention. FIG. 2A is a side view showing the punching apparatus for use in dispensing. FIG. 2B is an enlarged sectional view showing a blade portion of an ultrasonic cutter incorporated in the punching apparatus for use in dispensing. FIG. 3A is a plan view showing a plug body targeted to be applied by the punching apparatus for use in dispensing. FIG. 3B is a side view showing the plug body.

As shown in FIG. 1, a test tube 11 serving as a specimen container for housing a blood specimen S is made of a transparent glass, and is formed in the shape of a bottomed cylinder. An elastic plug body 12 made of a rubber or a synthetic resin material is mounted in a top opening 11a of the test tube 11.

The plug body 12 is cylindrically shaped. Its lower half is formed at a small diameter portion 12a inserted into the test tube 11, and its upper half is formed at a large diameter portion 12b which projects at the upper part of the test tube 11.

A stepped portion 12c abutting the opening edge of the test tube 11 is formed at the boundary between the small diameter portion 12a and the large diameter portion 12b. Further, on the bottom face of the plug body 12, a recessed portion 12d is concentrically provided to be recessed so that the small diameter portion 12a is easily elastically deformed in its tapered shape.

The test tubes 11 are held by a test tube holder 13 on a one-by-one basis. The test tube holder 13 has, for example, a holder main body 14 molded of a synthetic resin material. At the holder main body 14, an engagement portion is provided so as to be transported while it is held in a vertical state by a guide rail 15 serving as a transport passage. In the present embodiment, a ring shaped groove 14c is provided between upper and lower two-stepped flange portions 14a and 14b.

The guide rail 15 is formed in a channel shape formed of a synthetic resin material or an aluminum material, etc., and its cross section is formed in a U shape of a top opening. On the inner face of the guide rail 15, a guide rib 16 engaged with a ring shaped groove 14c of the holder main body 14 is provided over a longitudinal direction of the guide rail 15. A transport belt 17 composed of an endless belt is overhung so as to arbitrarily travel at the bottom part of the guide rail 15. The bottom face of the test tube holder 13 held on the guide rail 15 comes into contact with the top face of the transport belt 17 so that the test tube holder 13 is transported by means of friction.

A punch position P for use in punching the plug body 12 is provided in the middle of the guide rail 15. At this punch position P, a clamp 18 for temporarily pinching the test tube holder 13 to stop transport of the test tube 11 is provided. Further, a sensor 19 for sensing the height of the plug body 12 mounted on the test tube 11 is provided at the punch position P. The sensor 19 is provided as an optical sensor which includes, for example, a light emitting element 20 and a light receiving element 21. The sensor 19 senses the top face level of the plug body 12, so that a sense signal is input to a controller 22.

Further, an elevating mechanism 23 is provided at the punch position P. The elevating mechanism 23 comprises a drive mechanism 24 which includes, for example, a servo motor and a ball screw controlled by the controller 22. By means of the drive mechanism 24, an elevating member 25 is supported in a vertical state so as to be elevated as shown in FIG. 2A. At an upper end part of the elevating member 25, an ultrasonic cutter 27 is fixed vertically downwardly by a bracket 26.

The ultrasonic cutter 27 is mounted at the distal end part of a main body portion 28 which incorporates an ultrasonic vibrating portion, and is tapered. The ultrasonic cutter is structured to have a blade portion 29 which is formed in a cross shape at a transverse cross section of a sharpened end portion. The ultrasonic vibrating portion is connected to an ultrasonic oscillator 31 via a cable 30. Then, when the ultrasonic cutter 27 is lowered by the drive mechanism 24 in a state in which the cutter is ultrasonically vibrated, and the blade portion 29 of the ultrasonic cutter 27 is punched downwardly from the top face of the plug body 12, a dispensing hole 32 is punched on the plug body 12, as shown in FIG. 3A by ultrasonic vibration of the ultrasonic cutter 27.

Now, a functional description will be given with respect to the punching apparatus for use in dispensing, which is configured as described above. The test tube 11 held in a vertical state on the guide rail 15 via the test tube holder 13 is transported in the direction indicated by the arrow in FIG. 2A by the transport belt 17. When the test tube 11 reaches the punch position P, the test tube holder 13 is pinched by the clamp 18, and transport of the test tube 11 is temporarily stopped.

At this time, the upper face level of the plug body 12 of the test tube 11 is sensed by the sensor 19, and the sense signal is input to the controller 22. The controller 22 drives the drive mechanism 24 based on the sense signal input from the sensor 19. That is, the upper face level of the plug body 12 of the test tube 11 is not always uniform. Consideration is given to, for example, deviation of the insert depth relevant to the test tube holder 13, dimensional deviation of the plug body 12 itself, or deviation of the attachment depth relevant to the test tube 11. Therefore, the upper face level of the plug body 12 is sensed for the test tubes 11 on a one-by-one basis, whereby the lowering quantity of the elevating member 25 can be set by the drive mechanism 24.

On the other hand, the ultrasonic cutter 27 ultrasonically vibrates in a vertical direction. When the blade portion 29 of the ultrasonic cutter 27 is punched downwardly from the top face of the plug body 12 together with the lowering of the elevating member 25, the dispensing hole 32 is punched in the plug body 12 by means of ultrasonic vibration of the ultrasonic cutter 27. At this time, the lowering quantity of the ultrasonic cutter 27 is controlled by the controller 22 so as to set a stroke which stops immediately before penetrating the plug body 12. Thus, as shown in FIG. 3B, the dispensing hole 32 is provided as a bottomed hole on which a thickness portion "g" is left. Therefore, the chips caused when the ultrasonic cutter 27 is punched do not drop inside the test tube 11. In addition, even if the chips adhere to the blade portion 29 of the ultrasonic cutter 27, the following punching can be ready without washing out the chips from the blade portion.

When punching is terminated by the ultrasonic cutter 27, the elevating member 25 is elevated by the drive mechanism 24. Then, the clamp 18 is opened to release the test tube holder 13. Thus, the test tube 11 having the plug body 12 with the dispensing hole 32 punched therein is transported to the next process. Then, when the new test tube 11 is imported into the punch position P, the dispensing hole 32 is punched by repeating a similar action as described previously.

According to the foregoing embodiment, since the dispensing hole 32 is provided as a bottomed hole which does not penetrate the plug body 12, the chips caused when the ultrasonic cutter 27 is punched do not drop inside the test tube 11. Therefore, even if the chips adhere to the blade portion 29 of the ultrasonic cutter 27, there is no need for washing out the chips. A washing device is not required, and equipment can be simplified.

Further, although a description has been given with respect to a combination of a servo motor and a ball screw serving as the drive mechanism 24, a stepping motor may be used instead of the servo motor or elevation by an air cylinder may be carried out.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A punching method for use in dispensing, which punches dispensing holes on respective plug bodies of specimen containers closed by the plug bodies which are made of a rubber or synthetic resin material at an upper end opening of the specimen containers, the specimen containers having a blood specimen contained therein, the method comprising:

transporting one of the specimen containers along a transport passage to a punch position while the plug body thereof is held at the upper end;

setting a stroke of an ultrasonic cutter relative to the plug body such that the ultrasonic cutter stops immediately before penetrating the plug body;

when the plug body of the one specimen container reaches the punch position, punching by lowering the ultrasonic cutter according to the stroke set in the setting step from a top face thereof without penetrating the plug body to form a dispensing hole having a bottom;

raising the ultrasonic cutter;

transporting the one of the specimen containers along the transport passage away from the punch position;

transporting another of the specimen containers along the transport passage to the punch position while the plug body thereof is held at the upper end; and repeating the punching step on the other specimen container without washing out a chip caused in the punching step on the one specimen container.

2. A punching method for use in dispensing according to claim 1, further comprising:

sensing a height position of the plug body of the specimen container at the punch position;

wherein the setting step comprises setting a lowering quantity of the ultrasonic cutter based on the height position of the plug body obtained by the sensing.

3. A punching method for use in dispensing according to claim 1, wherein the ultrasonic cutter is formed in a cross shape at a transverse cross section of a sharpened end part thereof.

4. A punching method for use in dispensing according to claim 1, wherein the plug body is cylindrically shaped, a lower half of the plug body is formed at a small diameter portion inserted into the test tube, an upper half of the plug body is formed at a larger diameter portion projecting at the upper end of the test tube, a stepped portion abutting an opening edge of the test tube is formed at a boundary between the small diameter portion and the large diameter portion, and a recessed portion is concentrically provided with the small diameter portion at a lower surface of the plug body.

* * * * *